United States Patent
Chen et al.

(10) Patent No.: US 8,138,343 B2
(45) Date of Patent: Mar. 20, 2012

(54) CRYSTALLINE POLYMORPH OF 7-ETHYL-10-HYDROXYCAMPTOTHECIN

(75) Inventors: Shu-Ping Chen, Kaohsiung (TW); Piin-Jye Harn, Tainan (TW)

(73) Assignee: ScinoPharm Taiwan Ltd., Tainan County (TW)

(*) Notice: Subject to any disclaimer, the term of this patent is extended or adjusted under 35 U.S.C. 154(b) by 909 days.

(21) Appl. No.: 12/215,006

(22) Filed: Jun. 24, 2008

(65) Prior Publication Data

US 2009/0012111 A1     Jan. 8, 2009

Related U.S. Application Data

(60) Provisional application No. 60/937,098, filed on Jun. 25, 2007.

(51) Int. Cl.
*C07D 491/22* (2006.01)
(52) U.S. Cl. .......................................... 546/48
(58) Field of Classification Search ............ 546/48
See application file for complete search history.

(56) References Cited

U.S. PATENT DOCUMENTS

| 4,876,045 A | 10/1989 | Longo et al. |
| 4,990,635 A | 2/1991 | Longo et al. |
| 2006/0046993 A1 | 3/2006 | Forino et al. |

FOREIGN PATENT DOCUMENTS

| EP | 0074256 | 3/1983 |
| WO | WO01/04342 | 1/2001 |
| WO | WO2005/070951 | 8/2005 |
| WO | WO2005/117879 | 12/2005 |
| WO | WO2006082279 | 8/2006 |

OTHER PUBLICATIONS

Stewart, et al. Document No. 127:144742 (1997) retrieved from CAPLUS.*
Sawada, et al., Synthesis and Antitumor Activity of 20(S)-Camptothecin Derivatives: Carbamate-Linked, Water-Soluble Derivatives of 7-Ethyl-10-hydroxycamptothecin, Chem. Pharm. Bull 39(6) 1446-1454 (1991).
Kawato et al., Intracellular Roles of SN-38, a Metabolite of the Camptothecin Derivative CPT-11, in the Antitumor Effect of CPT-11, Cancer Research 51, 4187-4191 (1991).
European Search Report dated Jun. 22, 2011.

* cited by examiner

*Primary Examiner* — Shawquia Young

(57) ABSTRACT

A crystalline polymorph of 7-ethyl-10-hydroxycamptothecin exhibiting an X-ray diffraction pattern having peaks at 10.9±0.2, 13.2±0.2, 23.9±0.2, and 26.1±0.2 2-theta degree.

13 Claims, 2 Drawing Sheets

CRYSTALLINE POLYMORPH OF 7-ETHYL-10-HYDROXYCAMPTOTHECIN

RELATED APPLICATIONS

This application claims priority from U.S. Provisional Patent Application Ser. No. 60/937,098 which was filed on Jun. 25, 2007. The entire content of U.S. Provisional Patent Application Ser. No. 60/937,098 is incorporated herein as reference.

BACKGROUND OF THE INVENTION

1. Field of the Invention

The present invention relates to a novel crystalline form of 7-ethyl-10-hydroxycamptothecin, corresponding pharmaceutical compositions, methods of preparation and/or use thereof to treat anti-viral and/or cancer-related diseases.

2. Description of the Related Art

Irinotecan is a chemotherapy drug that is given as a treatment for certain types of cancer. It is most commonly used to treat bowel cancer. When administered to a patient, irinotecan metabolizes to a more active metabolite, 7-ethyl-10-hydroxycamptothecin, also known as SN38. SN38 itself is currently being studied as a chemotherapy drug, and has the following chemical structure.

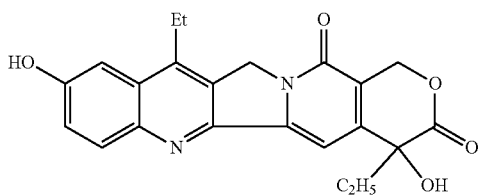

There is a need for developing an improved form of SN38, which is more suitable for pharmaceutical use.

SUMMARY OF THE INVENTION

We have discovered a novel crystalline form of SN38 and process of making the same.

In accordance with one embodiment of the present invention, the crystalline polymorph of SN38 exhibits an X-ray diffraction pattern having peaks at 10.9±0.2, 13.2±0.2, 23.9±0.2, and 26.1±0.2 2-theta degree.

Preferably, the X-ray diffraction pattern further has peaks at 10.4±0.2, 16.8±0.2, 17.7±0.2, 24.6±0.2, and 26.7±0.2 2-theta degree. More preferably, the X-ray diffraction pattern further has peaks at 12.9±0.2, 16.2±0.2, 17.6±0.2, 20.9±0.2, 22.3±0.2 and 33.3±0.2 2-theta degree.

In accordance with another embodiment of the present invention, the crystalline polymorph exhibits an X-ray diffraction pattern as depicted in FIG. 1.

In accordance with yet another embodiment of the present invention, the crystalline polymorph exhibits an infrared spectrum with bands at 3584±2 $cm^{-1}$, 3253±2 $cm^{-1}$, and 1736±2 $cm^{-1}$.

Preferably, the infrared spectrum additionally has bands at 1653±2 $cm^{-1}$, 1514±2 $cm^{-1}$, and 1173±2 $cm^{-1}$. More preferably, the crystalline polymorph has an infrared spectrum as depicted in FIG. 2.

The crystalline SN 38 discussed above in an effective amount can be incorporated with at least one pharmaceutically acceptable carrier to form a pharmaceutical composition.

In accordance with yet another embodiment of the present invention, we developed a process of making crystalline SN38, which comprises:

(1) dissolving crude SN38 with a solvent selected from the group consisting of acetic acid, dimethyl sulfoxide, N,N-dimethylacetamide, and mixtures thereof to form a solution;

(2) forming crystals of SN38 by adding an antisolvent selected from the group consisting of 1,2-dichloroethane, acetone, ethyl acetate, ethanol, and mixtures thereof to the solution of step 1) to obtain a slurry;

(3) filtering the slurry of step (2) to obtain the crystalline solid SN38.

Preferably, the dissolving step (1) is carried out at a temperature of at least 80 Celsius degree. The step 2) is conducted at a temperature of 0-30 Celsius degree.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

DETAILED DESCRIPTION OF THE PRESENTLY PREFERRED EMBODIMENTS

Figure 1:
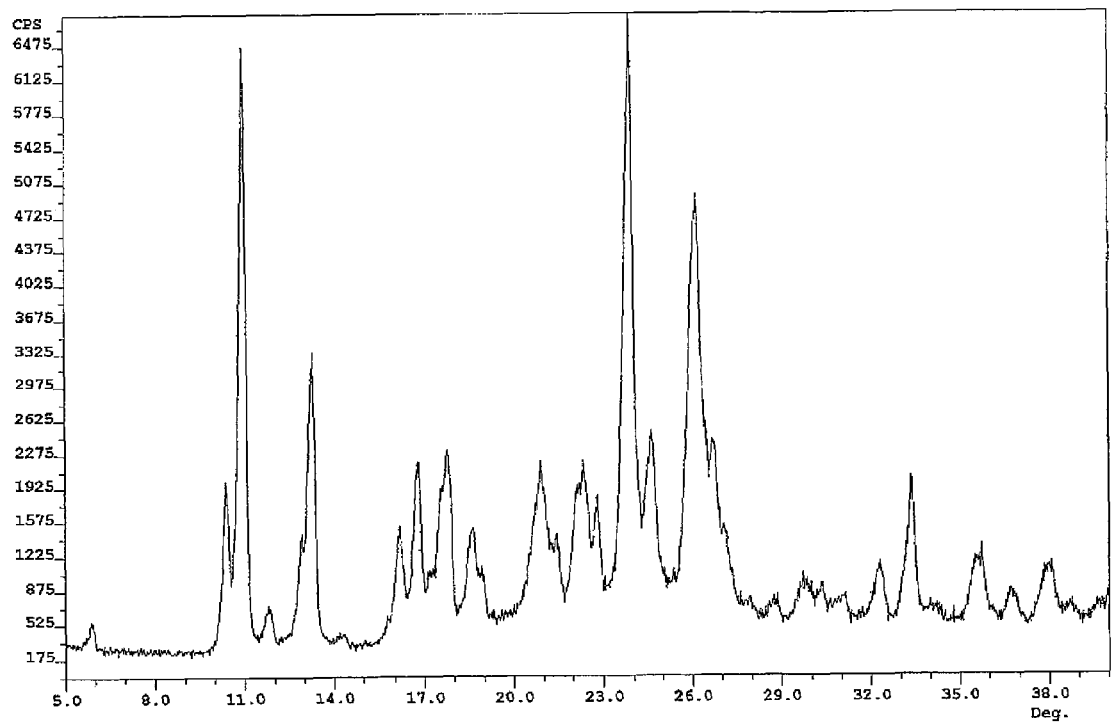
FIG. 1 shows an X-ray powder diffraction pattern exhibited by crystalline SN38 in accordance with one embodiment of the present invention.

The following examples are provided for illustrating, but not for limiting, the present invention.

Example 1

To a suitable reactor is charged SN38 (10.53 g) and Acetic acid (158 mL). The resulting slurry is heated to NLT 80° C. and agitated at NLT 80° C. till all of SN38 solids dissolved. When the mixture become to a clear solution, 1,2-dichloroethane (474 mL) is added slowly at NLT 75° C. After the addition is finished, the mixture is cooled to 20-30° C. and stir at this temperature for one hour. The solids are filtered and washed with 1,2-dichloroethane (53 mL). The solids are dried under vacuum at 50° C. and to give 6.51 g of SN38.

Example 2

To a suitable reactor is charged SN38 (39.3 g) and Acetic acid (585 mL). The resulting slurry is heated to NLT 80° C. and agitated at NLT 80° C. till all of SN38 solids dissolved. When the mixture become to a clear solution, ethyl acetate (1250 mL) is added slowly at NLT 75° C. After the addition is finished, the mixture is cooled to 0-10° C. and stir at this temperature for one hour. The solids are filtered and washed with ethyl acetate (160 mL). The solids are dried under vacuum at 50° C. and to give 34.95 g of SN38.

Example 3

To a suitable reactor is charged SN38 (0.5 g) and DMSO (5 mL). The resulting slurry is heated to NLT 80° C. and agitated at NLT 80° C. till all of SN38 solids dissolved.

When the mixture become to a clear solution, 1,2-dichloroethane (30 mL) is added slowly at NLT 75° C. After the addition is finished, the mixture is cooled to 0-10° C. and stir at this temperature for one hour. The solids are filtered and washed with 1,2-dichloroethane (15 mL). The solids are dried under vacuum at 50° C. and to give 0.15 g of SN38.

Example 4

To a suitable reactor is charged SN38 (0.5 g) and acetic acid (7.5 mL). The resulting slurry is heated to NLT 80° C. and agitated at NLT 80° C. till all of SN38 solids dissolved. The solution is cooled to 50° C. and acetone (10 mL) is added slowly at NLT 50° C. After the addition is finished, the mixture is cooled to 0-10° C. and stir at this temperature for one hour. The solids are filtered and washed with acetone (10 mL). The solids are dried under vacuum at 50° C. and to give 0.44 g of SN38.

Example 5

To a suitable reactor is charged SN38 (0.5 g) and N,N-dimethylacetamide (4 mL). The resulting slurry is heated to NLT 80° C. and agitated at NLT 80° C. till all of SN38 solids dissolved. The solution is cooled to 35° C. and dichloromethane (15 mL) is added slowly at NLT 35° C. After the addition is finished, the mixture is cooled to 0-10° C. and stir at this temperature for one hour. The solids are filtered and washed with dichloromethane (10 mL). The solids are dried under vacuum at 50° C. and to give 0.46 g of SN38.

Example 6

To a suitable reactor is charged SN38 (0.5 g) and Acetic acid (7.5 mL). The resulting slurry is heated to NLT 80° C. and agitated at NLT 80° C. till all of SN38 solids dissolved. When the mixture become to a clear solution, ethanol (22.5 mL) is added slowly at NLT 70° C. After the addition is finished, the mixture is cooled to 20-30° C. and stir at this temperature for one hour. The solids are filtered and washed with ethanol (10 mL). The solids are dried under vacuum at 50° C. and to give 0.40 g of SN38.

Figure 2:
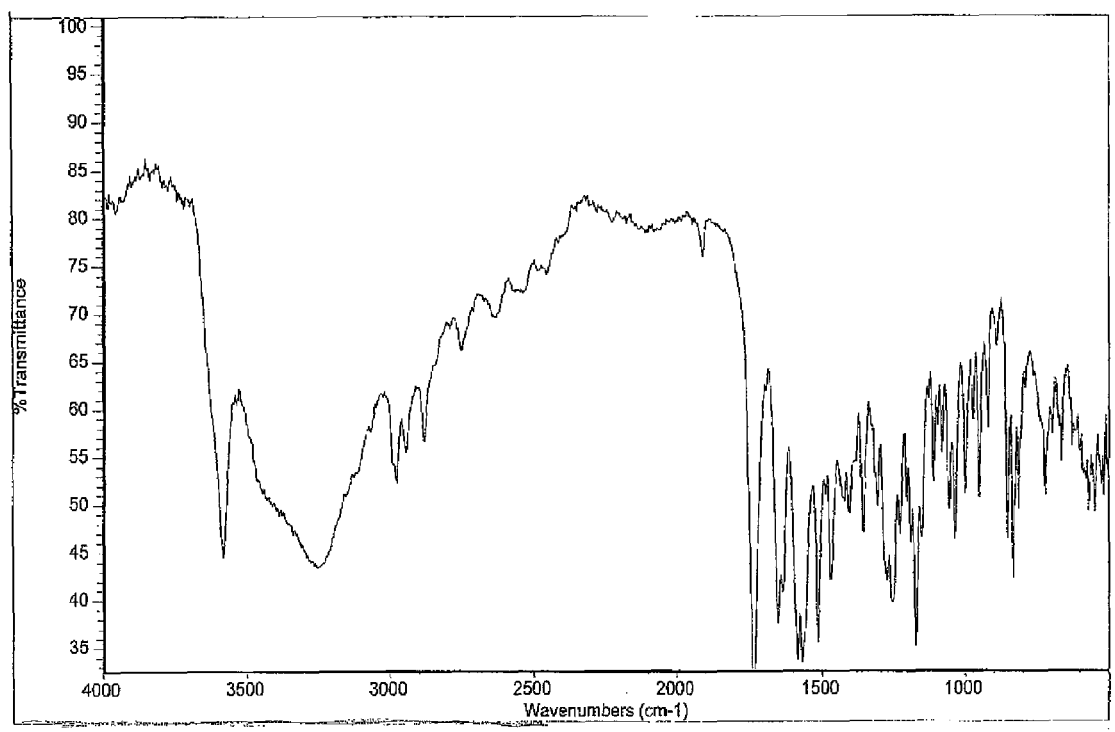
FIG. 2 shows an infrared spectrum exhibited by crystalline SN38 in accordance with one embodiment of the present invention.

SN38 obtained in each of the above examples exhibits an X-ray diffraction pattern as shown in FIG. 1 and an infrared spectrum as shown in FIG. 2.

The procedure of XRD test used for obtaining FIG. 1 is as follows. The test sample was milled and homogenously put on the tray of the X-ray machine, Scintag X2 Advance Diffraction, tested at continuous scan rate of 2.00 Deg/min, with range 5.00-40.00(Deg.) and at a wavelength of 1.540562.

The procedure of IR test used for obtaining FIG. 2 is as follows. We weighed about 3 mg of sample and disperse the sample homogenously in 300 mg dry KBr, and then, immediately recorded the spectrum between 400 to 4000 $cm^{-1}$ by diffuse reflectance. We performed a single test on the sample. The IR machine was Nicolet, Magna-IR 560 Spectrometer. The number of sample scans was 32. The number of background scans was 32. The resolution was 4. The sample gain was 8. The mirror velocity was 0.6329. The aperture was 100.

Our study also showed that the crystalline SN38 product prepared in accordance with the above examples was stable under the condition of 25° C. and 70% relative humidity for one year.

The invention is not limited by the embodiments described above which are presented as examples only but can be modified in various ways within the scope of protection defined by the appended patent claims.

We claim:

1. A crystalline polymorph of 7-ethyl-10-hydroxycamptothecin exhibiting an X-ray diffraction pattern having peaks at 10.9±0.2, 13.2±0.2, 23.9±0.2, and 26.1±0.2 2-theta degree.

2. The crystalline polymorph of claim 1 wherein the X-ray diffraction pattern further has peaks at 10.4±0.2, 16.8±0.2, 17.7±0.2, 24.6±0.2, and 26.7±0.2 2-theta degree.

3. The crystalline polymorph of claim 1 wherein the X-ray diffraction pattern further has peaks at 12.9±0.2, 16.2±0.2, 17.6±0.2, 20.9±0.2, 22.3±0.2, and 33.3±0.2 2-theta degree.

4. The crystalline polymorph of claim 1 wherein the X-ray diffraction pattern is depicted in FIG. 1.

5. The crystalline polymorph of claim 1 exhibiting an infrared spectrum with bands at 3584±2 cm−1, 3253±2 cm−1, and 1736±2 cm−1.

6. The crystalline polymorph of claim 5 wherein the infrared spectrum additionally has bands at 1653±2 cm−1, 1514±2 cm−1, and 1173±2 cm−1.

7. The crystalline polymorph of claim 5 wherein the infrared spectrum is depicted in FIG. 2.

8. A process of making crystalline 7-ethyl-10-hydroxycamptothecin comprising:
    (1) dissolving crude 7-ethyl-10-hydroxycamptothecin with a solvent selected from the group consisting of acetic acid, dimethyl sulfoxide, N,N-dimethylacetamide and mixtures thereof to form a solution;
    (2) forming crystals of 7-ethyl-10-hydroxycamptothecin by adding an antisolvent selected from the group consisting of 1,2-dichloroethane, acetone, ethyl acetate, ethanol, and mixtures thereof to the solution of step 1) to obtain a slurry;
    (3) filtering the slurry of step (2) to obtain the crystalline solid 7-ethyl-10-hydroxycamptothecin.

9. The process of claim 8 wherein the dissolving is carried out at a temperature of at least 80 degree Celsius.

10. The process of claim 8 wherein the step 2) is conducted at a temperature of 0-30 degree Celsius.

11. The process of claim 8 wherein the solvent is acetic acid, the antisolvent is selected from the group consisting of 1,2-dichloroethane, ethanol, and mixture thereof, and the step 2) is conducted at a temperature of 20-30 degree Celsius.

12. The process of claim 8 wherein the solvent is selected from the group consisting of acetic acid, dimethyl sulfoxide, N,N-dimethylacetamide, and mixtures thereof, the antisolvent is selected from the group consisting of ethyl acetate, acetone, 1,2-dichloroethane, and mixtures thereof, and the step 2) is conducted at a temperature of 0-10 degree Celsius.

13. A pharmaceutical composition comprising an effective amount of the crystalline polymorph of 7-ethyl-10-hydroxycamptothecin of claim 1 and at least one pharmaceutically acceptable carrier.

* * * * *

(12) EX PARTE REEXAMINATION CERTIFICATE (10209th)
United States Patent
Chen et al.

(10) Number: US 8,138,343 C1
(45) Certificate Issued: Jun. 27, 2014

(54) CRYSTALLINE POLYMORPH OF 7-ETHYL-10-HYDROXYCAMPTOTHECIN

(75) Inventors: Shu-Ping Chen, Kaohsiung (TW); Piin-Jye Harn, Tainan (TW)

(73) Assignee: ScinoPharm Taiwan Ltd., Tainan Science-Based Industrial Park, Tainan County (TW)

Reexamination Request:
No. 90/012,998, Sep. 13, 2013

Reexamination Certificate for:
Patent No.: 8,138,343
Issued: Mar. 20, 2012
Appl. No.: 12/215,006
Filed: Jun. 24, 2008

Related U.S. Application Data

(60) Provisional application No. 60/937,098, filed on Jun. 25, 2007.

(51) Int. Cl.
*C07D 491/22* (2006.01)
*C07D 491/147* (2006.01)

(52) U.S. Cl.
CPC ................................. *C07D 491/147* (2013.01)
USPC ............................................................ 546/48

(58) Field of Classification Search
None
See application file for complete search history.

(56) References Cited

To view the complete listing of prior art documents cited during the proceeding for Reexamination Control Number 90/012,998, please refer to the USPTO's public Patent Application Information Retrieval (PAIR) system under the Display References tab.

*Primary Examiner* — Evelyn Huang

(57) ABSTRACT

A crystalline polymorph of 7-ethyl-10-hydroxycamptothecin exhibiting an X-ray diffraction pattern having peaks at 10.9±0.2, 13.2±0.2, 23.9±0.2, and 26.1±0.2 2-theta degree.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-7 and 13 is confirmed.

Claims 8, 11 and 12 are determined to be patentable as amended.

Claims 9 and 10, dependent on an amended claim, are determined to be patentable.

New claims 14-18 are added and determined to be patentable.

8. A process of making crystalline 7-ethyl-10-hydroxycamptothecin comprising:
  (1) dissolving crude *solid* 7-ethyl-10-hydroxycamptothecin with a solvent selected from the group consisting of acetic acid, dimethyl sulfoxide, N,N-dimethylacetamide and mixtures thereof to form a solution;
  (2) forming crystals of 7-ethyl-10-hydroxycamptothecin by adding an antisolvent selected from the group consisting of 1,2-dichloroethane, acetone, ethyl acetate, [ethanol,] and mixtures thereof to the solution of step 1) to obtain a slurry;
  (3) filtering the slurry of step (2) to obtain the crystalline solid 7-ethyl-10-hydroxycamptothecin.

11. The process of claim 8 wherein the solvent is acetic acid, the antisolvent is [selected from the group consisting of] 1,2-dichloroethane, [ethanol, and mixture thereof,] and the step 2) is conducted at a temperature of 20-30 degree Celsius.

12. The process of claim 8 wherein [the solvent is selected from the group consisting of acetic acid, dimethyl sulfoxide, N,N-dimethylacetamide, and mixtures thereof, the antisolvent is selected from the group consisting of ethyl acetate, acetone, 1,2-dichloroethane, and mixtures thereof, and] the step 2) is conducted at a temperature of 0-10 degree Celsius.

*14. The process of claim 8 wherein the solvent is acetic acid, and the antisolvent is ethyl acetate.*

*15. The process of claim 8 wherein the solvent is N,N-dimethylacetamide, and the antisolvent is 1,2-dichloroethane.*

*16. The process of claim 8 wherein the solvent is acetic acid, and the antisolvent is 1,2-dichloroethane.*

*17. The process of claim 8 wherein the solvent is dimethyl sulfoxide, and the antisolvent is 1,2-dichloroethane.*

*18. The process of claim 8 wherein the solvent is acetic acid, and the antisolvent is acetone.*

\* \* \* \* \*